United States Patent
Utschig et al.

(10) Patent No.: US 7,798,476 B2
(45) Date of Patent: Sep. 21, 2010

(54) SHOCK ABSORBER FOR MEDICAL IMAGING DEVICE

(75) Inventors: Michael John Utschig, Wauwatoso, WI (US); Kenneth Scott Kump, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 878 days.

(21) Appl. No.: 11/325,097

(22) Filed: Jan. 3, 2006

(65) Prior Publication Data

US 2007/0152388 A1    Jul. 5, 2007

(51) Int. Cl.
*F16M 1/00*    (2006.01)

(52) U.S. Cl. .................................. 267/136; 250/370.09

(58) Field of Classification Search ............. 188/250 B, 188/251 M, 73.36–73.38, 158–160; 250/370.09; 267/136, 137
See application file for complete search history.

(56) References Cited

U.S. PATENT DOCUMENTS

| | | | | |
|---|---|---|---|---|
| 2,595,135 A | * | 4/1952 | Greenslade | 248/569 |
| 3,477,551 A | * | 11/1969 | Beuchle et al. | 188/250 B |
| 3,490,563 A | * | 1/1970 | Hahm | 188/73.37 |
| 3,563,347 A | * | 2/1971 | Hahm | 188/73.1 |
| 4,154,322 A | * | 5/1979 | Yamamoto et al. | 188/73.37 |
| 5,875,873 A | * | 3/1999 | Kay et al. | 188/73.38 |
| 5,975,252 A | * | 11/1999 | Suzuki et al. | 188/73.1 |
| 6,283,258 B1 | * | 9/2001 | Chen et al. | 188/250 E |
| 6,465,110 B1 | * | 10/2002 | Boss et al. | 428/608 |
| 6,564,909 B1 | * | 5/2003 | Razzano | 188/1.11 L |
| 6,700,126 B2 | | 3/2004 | Watanabe | |
| 7,175,007 B2 | * | 2/2007 | Roberts | 188/250 B |
| 2002/0181661 A1 | | 12/2002 | Vafi et al. | |
| 2006/0006339 A1 | * | 1/2006 | Fraser et al. | 250/372 |
| 2007/0085015 A1 | * | 4/2007 | Castleberry | 250/370.09 |

* cited by examiner

*Primary Examiner*—Christopher P Schwartz
(74) *Attorney, Agent, or Firm*—Armstrong Teasdale LLP

(57) ABSTRACT

Various embodiments of the invention provide a shock absorber. The shock absorber comprising a frame having three sides, namely a first side, a second side and a third side. The first side is contiguous with the second side, which is contiguous with the third side. Further, the first side makes an angle greater than zero degrees with the second side and the second side makes an angle greater than zero degrees with the third side. The frame is different from a housing.

7 Claims, 10 Drawing Sheets

SHOCK ABSORBER FOR MEDICAL IMAGING DEVICE

BACKGROUND OF THE INVENTION

This invention relates generally to shock-absorbing systems, and more particularly, to a shock absorber for a portable medical imaging device.

When providing medical care to patients located at remote locations or under certain conditions where the patient cannot be moved to a hospital, a portable medical device is used. One such portable medical imaging device is a portable X-ray detector. The portable medical imaging device includes a plurality of electronic components and detects radiations, such as, x-rays and gamma rays. The electronic components may be a scintillator array, a photodetector array, and a cable coupled to the photodetector array. An example of the photodetector array includes a photodiode array. The substrate of these arrays is typically glass. The presence of the electronic components and the glass substrate makes the portable medical imaging device fragile and vulnerable to damage.

BRIEF DESCRIPTION OF THE INVENTION

Various embodiments of the invention provide a shock absorber. The shock absorber includes a frame having three sides, namely a first side, a second side and a third side. The first side is contiguous with the second side which, in turn, is contiguous with the third side. Further, the first side makes an angle greater than zero degrees with the second side and the second side makes an angle greater than zero degrees with the third side. The frame is different from a housing.

DETAILED DESCRIPTION OF THE INVENTION

A shock absorber including a frame with three sides to protect a portable medical imaging device has been described. The shock absorber may be fabricated from, for example, a plastic, an elastomer, or a metal. The shock absorber includes a frame, wherein the frame further includes a first side, a second side, and a third side. The sides of the shock absorber are at an angle greater than zero degrees from each other and are contiguous with each other. The shock absorber is different from a housing of the medical imaging device. Examples of medical imaging devices include, but are not limited to, an X-Ray detector, a CT detector, a gamma ray detector, and any other imaging device having a housing.

Figure 1:
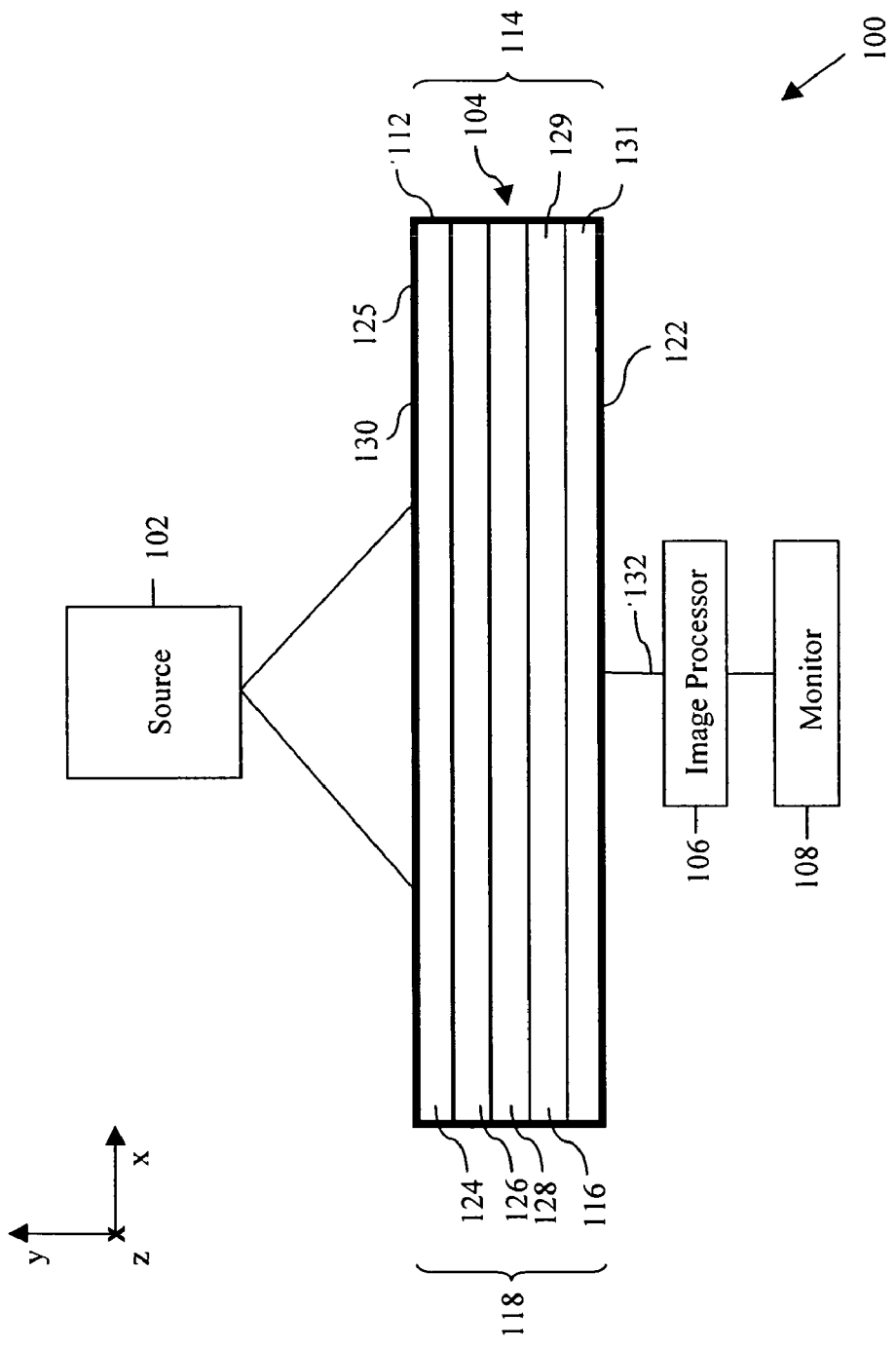
FIG. 1 is a diagram illustrating a portable medical imaging system, in accordance with various embodiments of the invention.

FIG. 1 is a diagram illustrating a medical imaging system 100, in accordance with various embodiments of the invention. Medical imaging system 100 includes a source 102, such as an x-ray tube or a gamma ray source. Medical imaging system 100 further includes a portable detector 104, such as an x-ray detector or a gamma ray detector. Medical imaging system 100 also includes an image processor 106 and a monitor 108. A housing 112, represented by a bold line, of detector 104 includes a plurality of sides 114, 116, 118, 120, a bottom side 122, and a top side 125. Housing 112 also includes a cover 130. The detector 104 may further include a scintillator array 124, a photodetector array 126, a substrate 128, such as a glass substrate, a structural layer 129, and a circuit board 131. Structural layer 128 provides support to arrays 124 and 126, and to substrate 128. Circuit board 131 includes circuitry for processing electrical signals from arrays 124 and 126. Examples of the circuitry include a circuit that provides power management of power consumed by detector 104, a circuit that generates calibration data, and a circuit that processes the electrical signals by digitizing and sampling the electrical signals. Housing 112 is made of a material, such as a metal or plastic. Side 120 is not visible in FIG. 1. Housing 112 protects detector 104 from an environmental pollutant, such as dust or debris, and from other materials, such as patient sweat and blood. Examples of photodetector array 126 include a photodiode array.

Source 102 generates radiation, such as x-rays or gamma rays that passes through a subject, such as a patient, and is detected by detector 104. The radiation passes through top side 125 into the arrays 124 and 126 which convert the visible light into the electrical signals that are processed by circuit board 131 and that are received via a link 132 by image processor 106. Link 132 may be a wire or alternatively a wireless connection. If link 132 is a wireless connection, housing 112 includes a radio frequency (RF) transmitter and image processor 106 is coupled to RF transmitter via an RF receiver. Image processor 106 receives the electrical signals to generate an image, such as an x-ray image or a gamma ray image, which is displayed on monitor 108.

Figure 2:
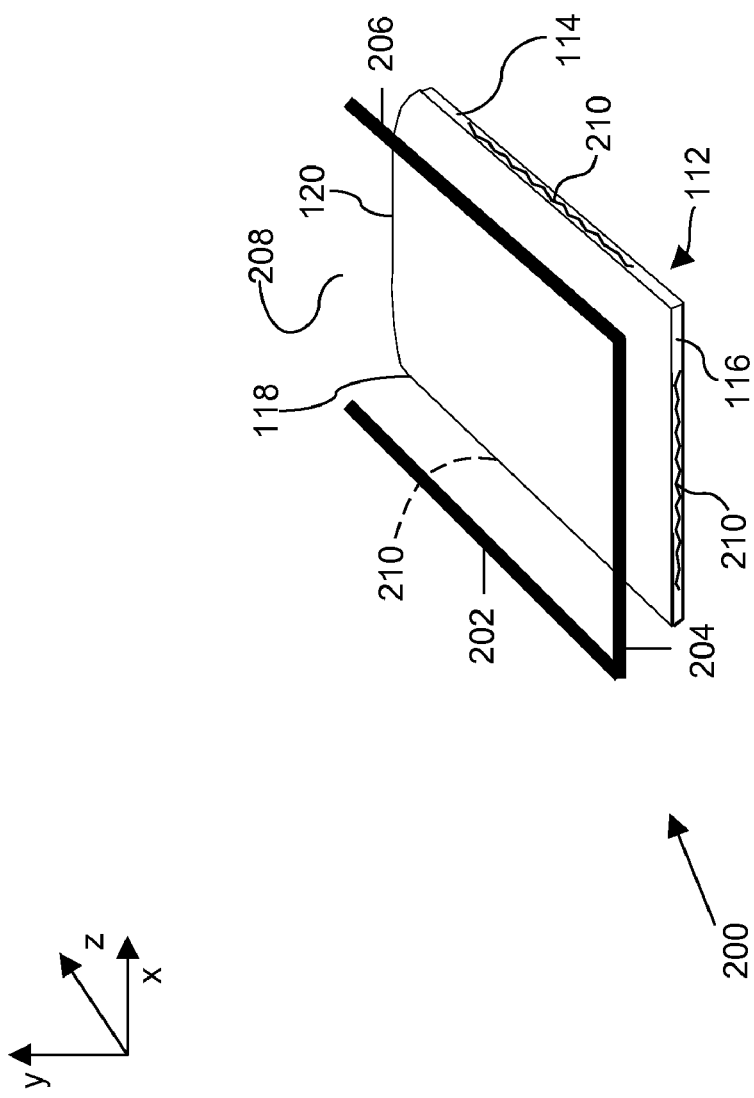
FIG. 2 is a diagram illustrating a shock absorber including three sides, in accordance with an embodiment of the invention.

FIG. 2 is a diagram illustrating a shock absorber 200, in accordance with an embodiment of the invention. Shock absorber 200 is used for protecting detector 104. Shock absorber 200 includes three sides, namely a first side 202, a second side 204, and a third side 206. First side 202 is contiguous but not integral with second side 204, which, in turn, is contiguous but not integral with third side 206. A gap 208, such as an air gap, is formed between first side 202 and third side 206. In accordance with various embodiments of the invention, first side 202 makes an angle greater than zero degrees with second side 204, and second side 204 makes an angle greater than zero degrees with third side 206. For example, first side 202 makes an angle of 90 degrees with second side 204, and second side 204 makes an angle of 90 degrees with third side 206. Alternatively, first side 202 is integral with second side 204. In yet another alternative embodiment, second side 204 is integral with third side 206. In accordance with various embodiments of the invention, first side 202, second side 204, and third side 206 are made of a shock-absorbing material. Examples of the shock-absorbing material include, but are not limited to, a plastic and a metal, such as aluminum. Examples of the plastic include, but are not limited to, thermofoam, thermoplastic, acronitrile butadiene styrene (ABS), and high impact polystyrene (HIPS). In various embodiments of the invention, shock absorber 200 is fabricated by injection molding the shock-absorbing material.

Shock absorber 200 is fitted around housing 112 and held in place around housing 112 by friction 210 between shock absorber 200 and housing 112. Shock absorber 200 is fitted in such a manner that first side 202 is adjacent to side 118 of housing 112, second side 204 is adjacent to side 116 of housing 112, and third side 206 is adjacent to side 114 of housing 112. In various embodiments of the invention, shock absorber 200 is attached to housing 112 without use of any one of a mechanical tool, an electrical tool, and an adhesive. Examples of the mechanical tool include a screw and a bolt. Examples of the electrical tool include a drill machine and a hammer. In yet another alternative embodiment, shock absorber 200 is attached to housing 112 by using any one of the mechanical tool, the electrical tool, and the adhesive. When shock absorber 200 is separated from housing 112, first side 202 is not adjacent to side 118 of housing 112, second side 204 is not adjacent to side 116 of housing 112, and third side 206 is not adjacent to side 114 of housing 112.

Figure 3:
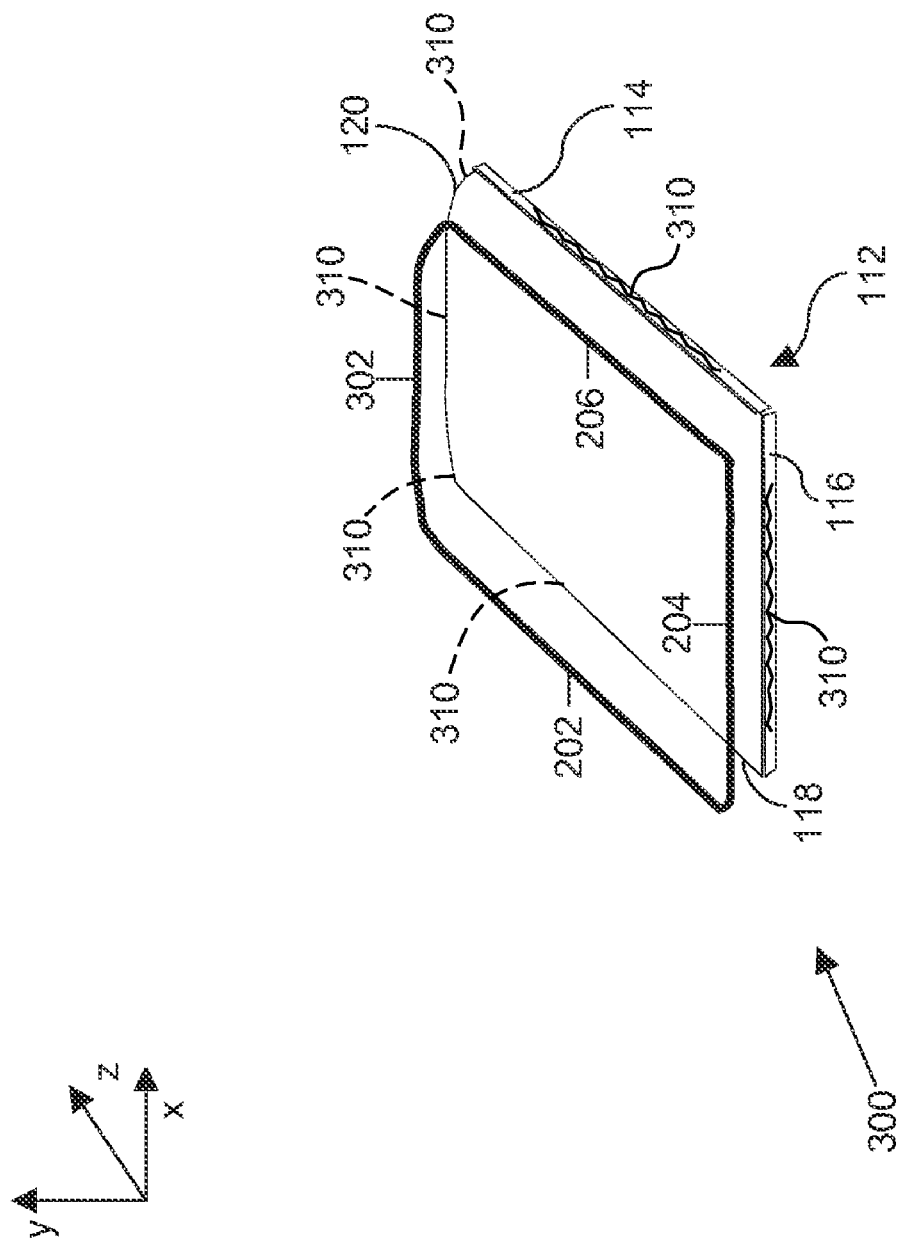
FIG. 3 is a diagram illustrating a shock absorber including four sides, in accordance with another embodiment of the invention.

FIG. 3 is a diagram illustrating a shock absorber 300, in accordance with an alternate embodiment of the invention. Shock absorber 300 includes first side 202, second side 204, third side 206, and a fourth side 302. Fourth side 302 is contiguous but not integral with first side 202 and third side 206. Alternatively, fourth side 302 is integral with first side 202 and third side 206. In accordance with an embodiment of the invention, fourth side 302 makes an angle greater than zero degrees with first side 202 and third side 206. For example, fourth side 302 makes an angle of 90 degrees with first side 202 and third side 206. Fourth side 302 is made of the shock-absorbing material. As an example, fourth side 302 is made by injection molding the shock-absorbing material. The addition of fourth side 302 to shock absorber 300 protects detector 104 on all four sides 114, 116, 118, and 120. Shock absorber 300 is fitted to surround housing 112 and held in place around housing 112 by friction 310 between shock absorber 300 and housing 112. Shock absorber 300 is fitted in such a manner that first side 202 is adjacent to side 118 of housing 112, second side 204 is adjacent to side 116 of housing 112, third side 206 is adjacent to side 114 of housing 112, and fourth side 302 is adjacent to side 120 of housing 112. In various embodiments of the invention, shock absorber 300 is attached to housing 112 without use of any one of the mechanical tool, the electrical tool, and the adhesive. In yet another alternative embodiment, shock absorber 300 is attached to housing 112 by using any one of the mechanical tool, the electrical tool, and the adhesive. When shock absorber 300 is separated from housing 112, first side 202 is not adjacent to side 118 of housing 112, second side 204 is not adjacent to side 116 of housing 112, third side 206 is not adjacent to side 114 of housing 112, and fourth side 302 is not adjacent to side 120 of housing 112.

Figure 4:
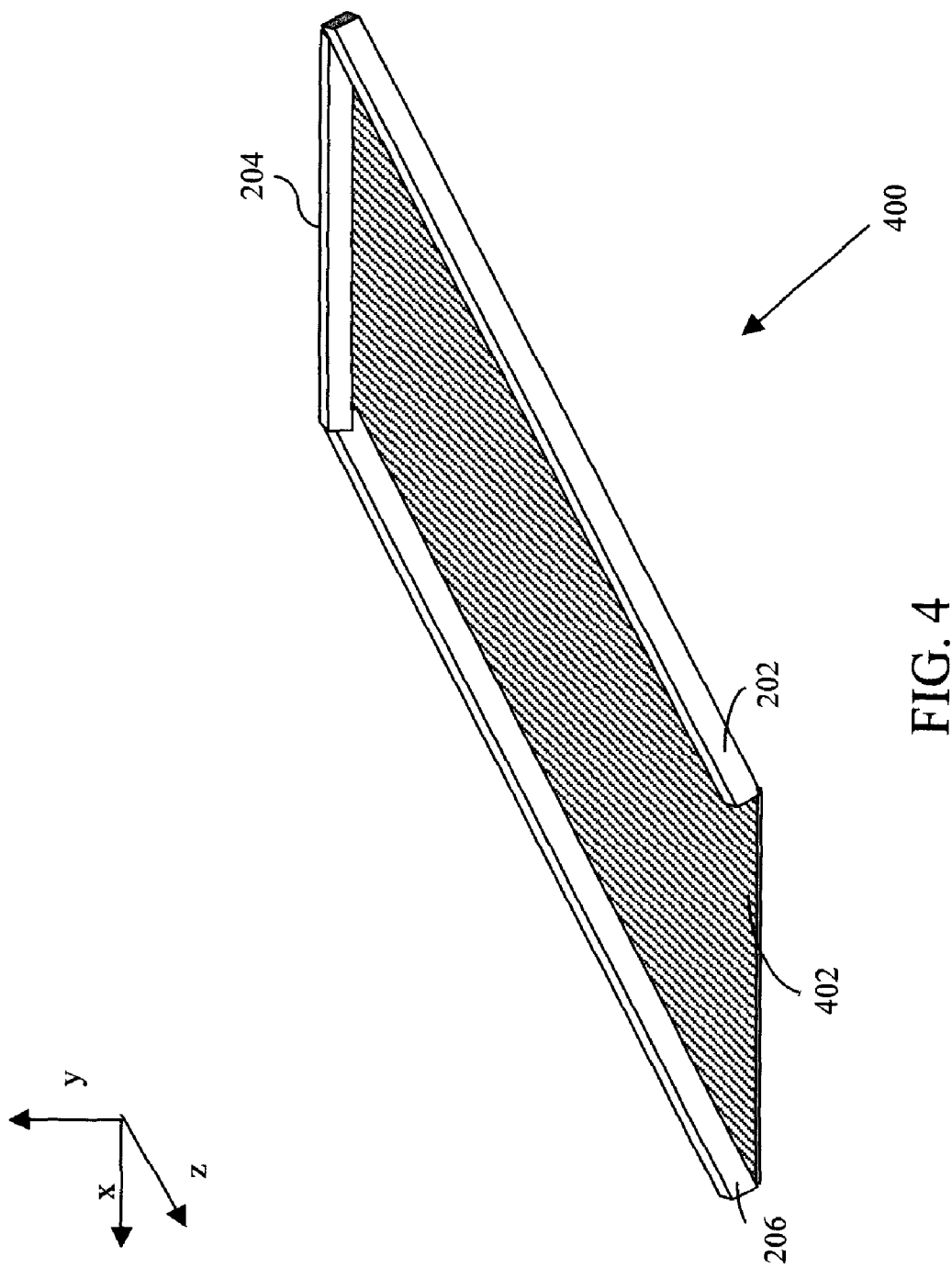
FIG. 4 is a diagram illustrating a shock absorber including a back, in accordance with an embodiment of the invention.

FIG. 4 is a diagram illustrating a shock absorber 400, in accordance with an alternate embodiment of the invention. In another embodiment of the invention, shock absorber 400 includes a back side 402. Back side 402 extends from first side 202 to third side 206 and from second side 204 to gap 208. First side 202, second side 204, and third side 206 of shock absorber 200 form an angle greater than zero degrees with back side 402, and are contiguous but not integral with back side 402. Alternatively, any one of first side 202, second side 204, and third side 206 is integral with back side 402. In an embodiment of the invention, back side 402 may be a continuous sheet of material. In an alternate embodiment of the invention, back side 402 may have a frame structure. Back side 402 is fabricated from the shock-absorbing material. The provision of back side 402 further enhances a shock-absorbing capacity of shock absorber 200.

Shock absorber 400 is fitted around housing 112 (shown in FIGS. 1-3) of detector 104 (shown in FIG. 1) and held in place by friction 410 between shock absorber 400 and housing 112. Shock absorber 400 is fitted in such a manner that first side 202 is adjacent to side 118 of housing 112, second side 204 is adjacent to side 116 of housing 112, third side 206 is adjacent to side 114 of housing 112, and back side 402 is adjacent to bottom side 122 of housing 112. Shock absorber 400 is attached to housing 112 without use of any one of the mechanical tool, the electrical tool, and the adhesive. In yet another alternative embodiment, shock absorber 400 is attached to housing 112 by using any one of the mechanical tool, the electrical tool, and the adhesive. When shock absorber 400 is separated from housing 112, first side 202 is not adjacent to side 118 of housing 112, second side 204 is not adjacent to side 116 of housing 112, third side 206 is not adjacent to side 114 of housing 112, and back side 402 is not adjacent to bottom side 122 of housing 112.

Figure 5:
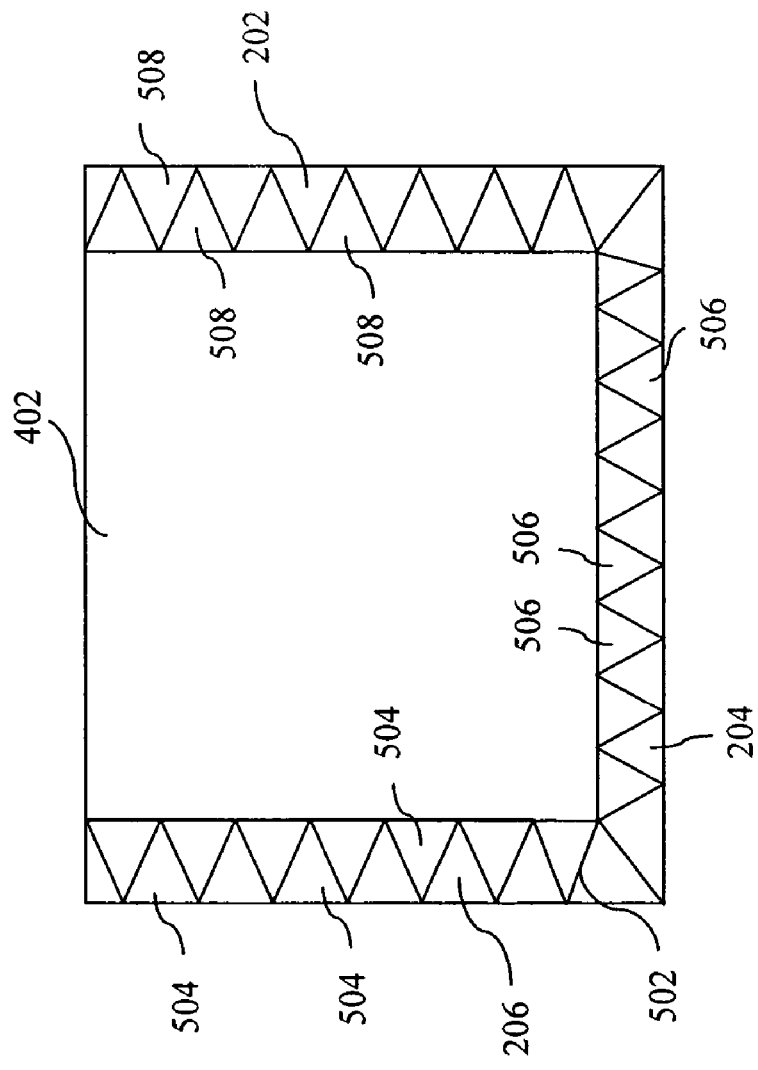
FIG. 5 is a diagram illustrating a plurality of integrally formed ribbed portions within a shock absorber, in accordance with an embodiment of the invention.
Figure 5:
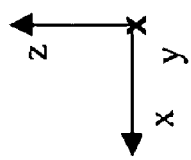

FIG. 5 is a diagram illustrating a ribbed pattern 502, including a plurality of ribbed portions, formed under first side 202, second side 204, and third side 206, in accordance with various embodiments of the invention. Ribbed pattern 502 extends along lengths of first side 202, second side 204, and third side 206. Ribbed pattern 502 may be fabricated from the shock-absorbing material by injection molding the shock-absorbing material. Ribbed pattern 502 may be attached, such as glued, integrally molded, or overmolded, to first side 202, second side 204, and third side 206. Alternatively, ribbed portion 502 is integral with at least one of first side 202, second side 204, and third side 206. In the alternative embodiment, ribbed pattern 502 is fabricated by etching away each portion 504 of first side 202, each portion 506 of second side 204, or etching away each portion 508 of third side 206. In an alternative embodiment of the invention, ribbed pattern 502 is formed within back side 402. In yet another alternative embodiment, ribbed pattern 502 is formed integral with a portion of at least one of first side 202, second side 204, third side 206, fourth side 302, and back side 402. In still another alternative embodiment, ribbed portion is formed under at least one of first side 202, second side 204, third side 206, fourth side 302, and back side 402. Ribbed pattern 502 gets deformed on application of pressure to ribbed pattern 502. The deformation enhances a shock-absorbing capacity of one of shock absorbers 200, 300, and 400 in which ribbed pattern 502 is formed.

Figure 6:
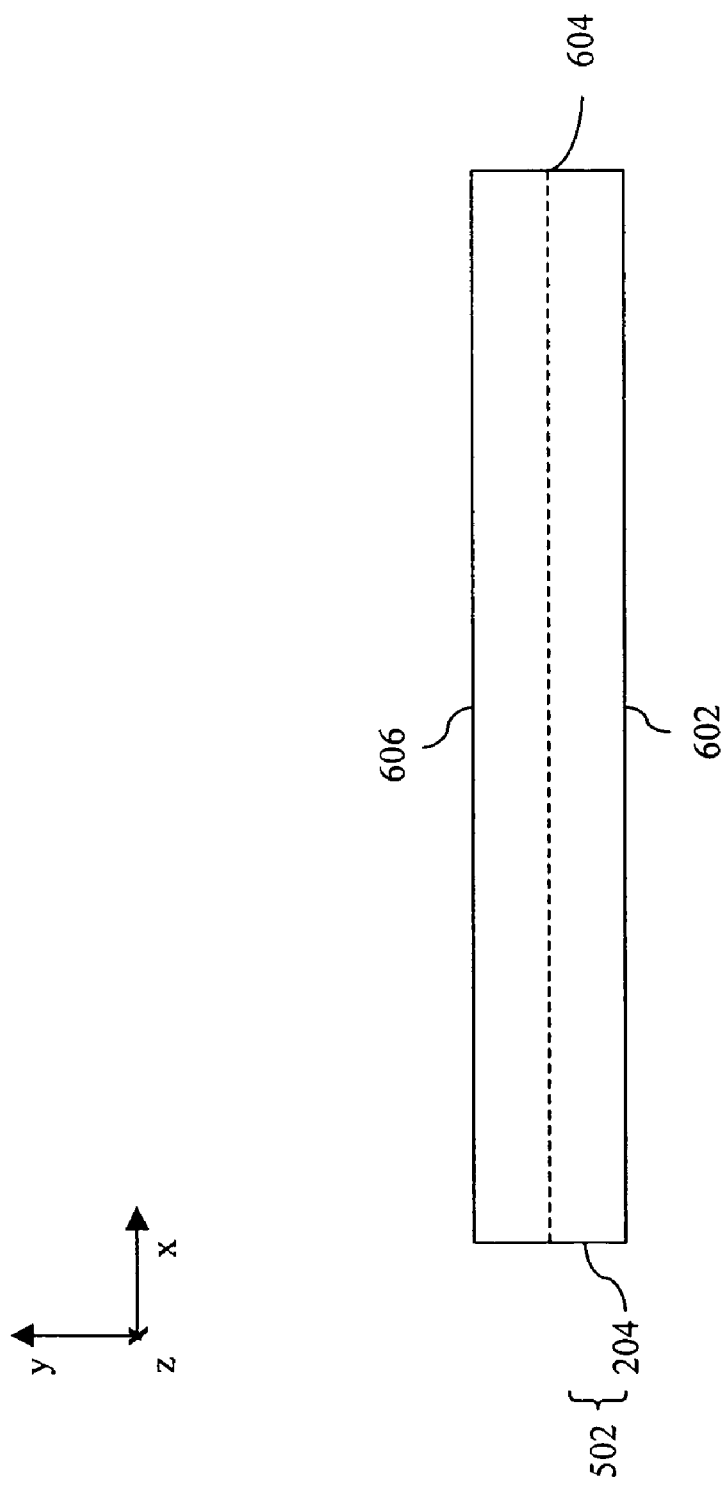
FIG. 6 is a diagram illustrating a side of a shock absorber, in accordance with various embodiments of the invention.

FIG. 6 is an embodiment of second side 204. Ribbed pattern 502 extends along a thickness measured along a y-direction of a y-axis. Ribbed pattern 502 extends from a bottom surface 602 of second side 204 to a point 604 intermediate between bottom surface 602 and a top surface 606 of second side 204. Bottom surface 602 is adjacent to back side 402. Alternatively, ribbed pattern 502 extends from top surface 606 to point 604. Similarly, in an alternative embodiment, ribbed pattern 502 extends along a thickness, along the y-direction, of a portion of at least one of first side 202, second side 204, third side 206, fourth side 302, and back side 402.

Figure 7:
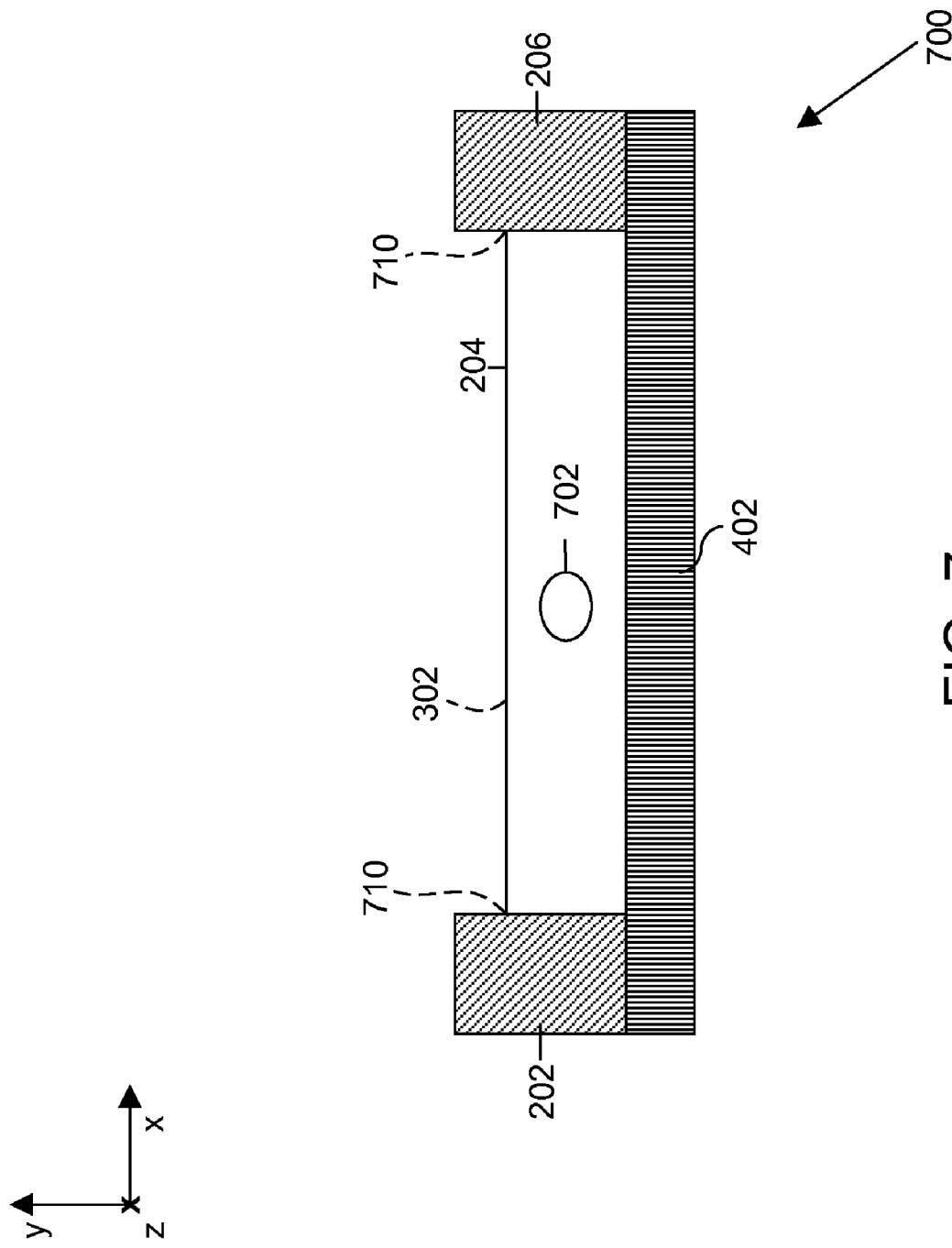
FIG. 7 is a diagram illustrating a notch on a side of a shock absorber, in accordance with an embodiment of the invention.

FIG. 7 is a diagram illustrating a cross-sectional view of a shock absorber 700, in accordance with various embodiments of the invention. Shock absorber 700 includes first side 202, second side 204, third side 206, fourth side 302, and back side 402. Back side 402 extends from first side 202 to third side 206 and from second side 204 to fourth side 302. Fourth side 302 is behind second side 204 and is not visible in FIG. 7. Fourth side 302 forms an angle greater than zero degrees with back side 402 and is contiguous but not integral with back side 402. Alternatively, fourth side 302 is integral with back side 402. Shock absorber 700 is fitted around housing 112 and held in place by friction 710 between shock absorber 700 and housing 112. Shock absorber 700 is fitted in such a manner that first side 202 is adjacent to side 118 of housing 112, second side 204 is adjacent to side 116 of housing 112, third side 206 is adjacent to side 114 of housing 112, fourth side 302 is adjacent to side 120 of housing 112, and back side 402 is adjacent to bottom side 122 of housing 112. Shock absorber 700 is attached to housing 112 without use of any one of the mechanical tool, the electrical tool, and the adhesive. In yet another alternative embodiment, shock absorber 700 is attached to housing 112 by using any one of the mechanical tool, the electrical tool, and the adhesive. When shock absorber 700 is separated from housing 112, first side 202 is not adjacent to side 118 of housing 112, second side 204 is not adjacent to side 116 of housing 112, third side 206 is not adjacent to side 114 of housing 112, fourth side 302 is not adjacent to side 120 of housing 112, and back side 402 is not adjacent to bottom side 122 of housing 112.

Housing 112 may be slid into shock absorber 700. A structure of shock absorber 700 helps in keeping housing 112 firm in shock absorber 700 because housing 112 is covered on sides 114, 116, 118, 120, and bottom side 122. Since housing 112 is covered on sides 114, 116, 118, 120, and bottom side 122, a notch 702 for link 132 is provided.

Notch 702 may be used to pass at least one wire to image processor 106 and/or to any other device. In various embodiments of the invention, notch 702 may be in any one of first side 202, third side 206, fourth side 302 and back side 402. The provision of notch 702 further helps in fitting housing 112 in shock absorber 700.

Figure 8:
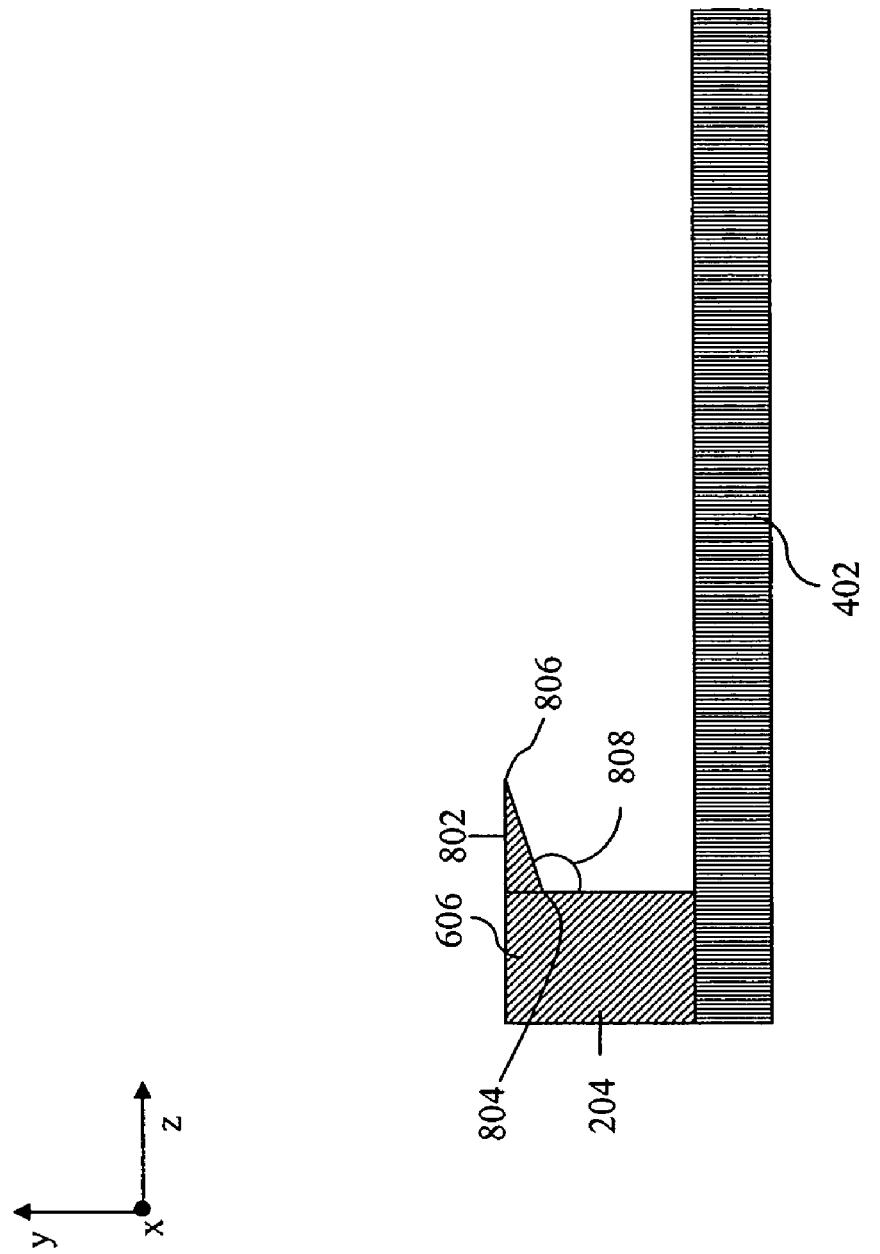
FIG. 8 is a diagram illustrating a protrusion on a side of a shock absorber, in accordance with an embodiment of the invention.

FIG. 8 is a diagram illustrating a protrusion 802 on second side 204, in accordance with an embodiment of the invention. In an alternate embodiment, protrusion 802 may be on at least one of first side 202, second side 204, third side 206, and fourth side 302. Protrusion 802 is made of the shock-absorbing material by injection molding, and is glued or alternatively bolted to shock absorber side 204. Alternatively, protrusion 802 is made of an elastomer, such as a silicon elastomer, rubber, or urethane. Alternately, protrusion 802 is a metal clip. The metal clip is made of exemplary materials such as brass and stainless steel. Examples of shapes of the metal clip include an S-shape and a spiral shape. In yet another alternative embodiment, protrusion 802 is integral with at least one of first side 202, second side 204, third side 206, and fourth side 302. Protrusion 802 extends from top surface 606 of second side 204 to a point 804 intermediate between top surface 606 and back side 402. Protrusion 802 extends from second side 204 to a point 806 intermediate between second side 204 and fourth side 302. Similarly, in an alternative embodiment, protrusion 802 extends from a top surface of one of first side 202, third side 206, and fourth side 302 to a point intermediate between back side 402 and the one of first side 202, third side 206, and fourth side 302. Moreover, similarly, in an alternative embodiment, protrusion 802 extends from any one of first side 202, third side 206, and fourth side 302 to a point intermediate between the one of first side 202, third side 206, and fourth side 302 and a remaining one of the first side 202, second side 204, third side 206, and fourth side 302 facing the one of the first side 202, third side 206, and fourth side 302.

Protrusion 802 forms an angle 808, between zero and ninety degrees, with second side 204. Similarly, in an alternative embodiment, protrusion 802 forms an angle, between zero and ninety degrees, with one of first side 202, third side 206, and fourth side 302. Housing 112 is slid into a shock absorber including protrusion 802 if protrusion 802 is made of the shock-absorbing material. If protrusion 802 is made of the elastomer, the shock absorber including protrusion 802 is slid on housing 112. Protrusion 802 helps retain housing 112 by extending over and adjacent to the top side 125. When the shock absorber including protrusion 802 is separated from housing 112, protrusion 802 does not extend over and is not adjacent to top side 125.

Figure 9:
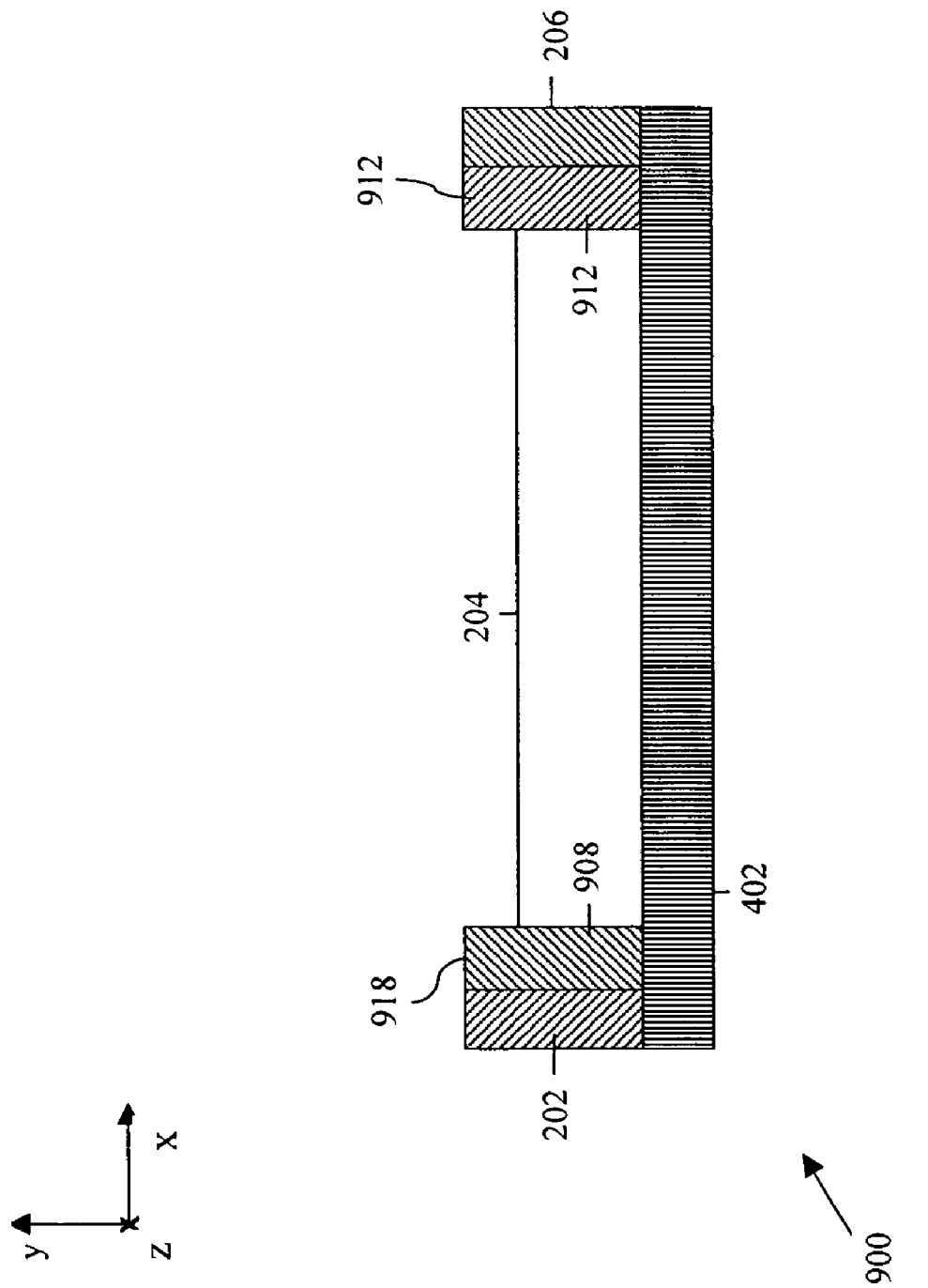
FIG. 9 is a diagram illustrating a cross-sectional view of a shock absorber with more than one layer of material, in accordance with an embodiment of the invention.
Figure 10:
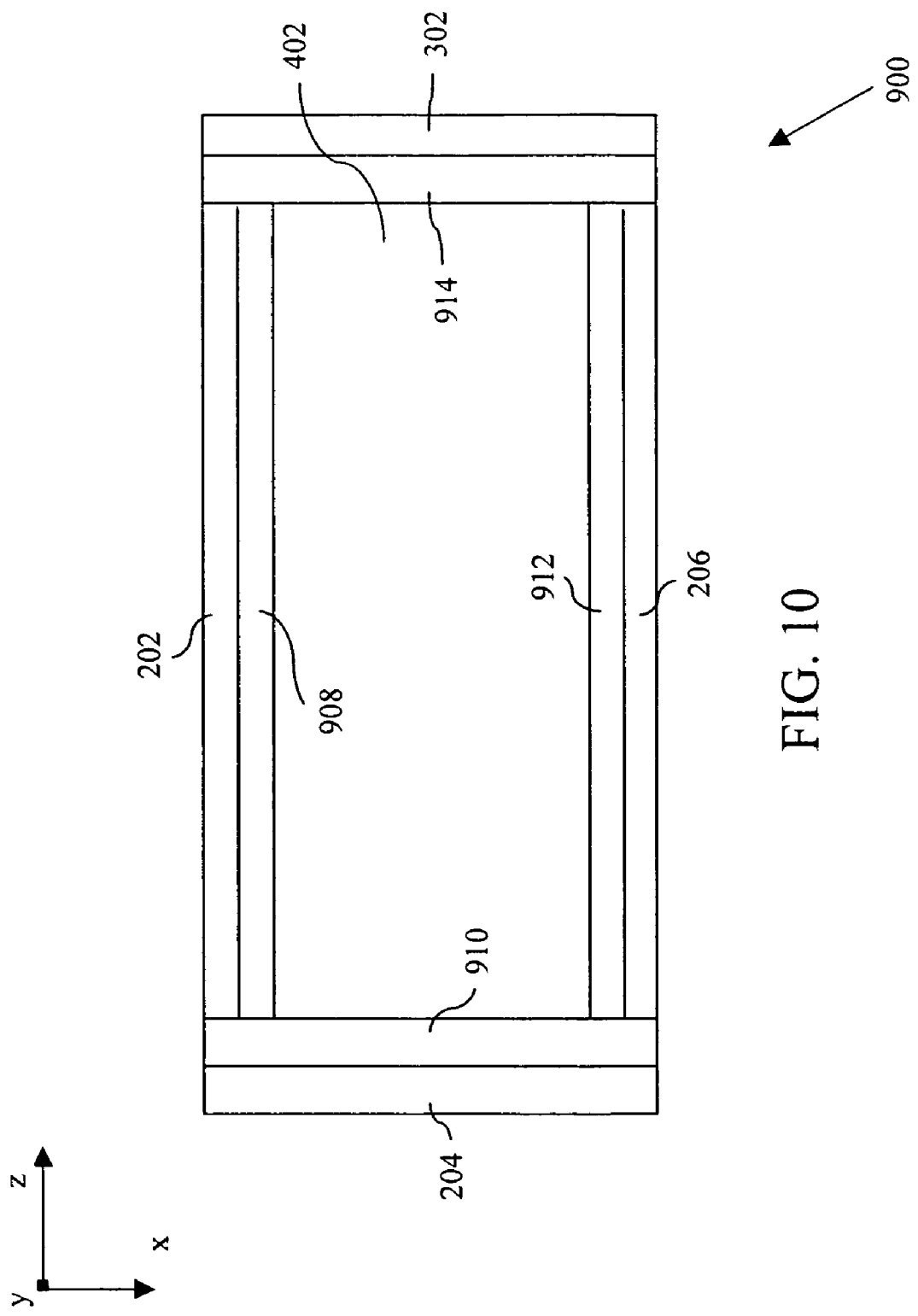
FIG. 10 is a diagram illustrating a top view of the shock absorber of FIG. 9.

FIGS. 9 and 10 illustrate a cross-sectional view of a shock absorber 900, in accordance with an embodiment of the invention. Shock absorber 900 includes first side 202, second side 204, third side 206, fourth side 302, a fifth side 908, a sixth side 910, a seventh side 912, and an eighth side 914. Shock absorber 900 further includes back side 402. Fifth side 908 is adjacent to first side 202. Sixth side 910 is adjacent to second side 204. Seventh side 912 is adjacent to third side 206. Eighth side 914 is adjacent to fourth side 302. Fifth side 908 forms an angle greater than zero degrees with sixth side 910. For example, fifth side 908 forms an angle of 90 degrees with sixth side 910. As another example, fifth side 908 forms the same angle, such as 89 degrees, with sixth side 910 as that formed by first side 902 with second side 904. Sixth side 910 forms an angle greater than zero degrees with seventh side 912. For example, sixth side 910 forms an angle of 90 degrees with seventh side 912. As another example, sixth side 910 forms the same angle, such as 88 degrees, with seventh side 912 as that formed by second side 204 with third side 206. Seventh side 912 forms an angle greater than zero degrees with eighth side 914. For example, seventh side 912 forms an angle of 90 degrees with eighth side 914. As another example, seventh side 912 forms the same angle, such as 86 degrees, with eighth side 914 as that formed by third side 206 with fourth side 302. Eighth side 914 forms an angle greater than zero degrees with fifth side 908. For example, eighth side 914 forms an angle of 90 degrees with fifth side 908. As another example, eighth side 914 forms the same angle with fifth side 908 as that formed by fourth side 302 with first side 202. Fifth side 908 is attached, such as coextruded, overmolded, glued, or bolted, to first side 202, and sixth side 910 is attached, such as coextruded, overmolded, glued, or bolted, to second side 204. Seventh side 912 is attached, such as coextruded, overmolded, glued, or bolted, to third side 206, and eighth side 914 is attached, such as coextruded, overmolded, glued, or bolted, to fourth side 302.

In an alternative embodiment, a number of sides are adjacent to fifth side 908. For example, an additional side is adjacent to fifth side 908, and fifth side 908 lies between the additional side and first side 202. In yet another alternative embodiment, a number of sides are adjacent to sixth side 910. For example, an additional side is adjacent to sixth side 910, and sixth side 910 lies between the additional side and second side 204. In still another alternative embodiment, a number of sides are adjacent to seventh side 912. For example, an additional side is adjacent to seventh side 912, and seventh side 912 lies between the additional side and third side 206. In another alternative embodiment, a number of sides are adjacent to eighth side 914. For example, an additional side is adjacent to eighth side 914, and eighth side 914 lies between the additional side and fourth side 302.

Fifth side 908, sixth side 910, seventh side 912, and eighth side 914 of shock absorber 900 may be fabricated by injection molding. In one embodiment, first side 202, second side 204, third side 206, and fourth side 302 are fabricated from the shock-absorbing material and fifth side 908, sixth side 910, seventh side 912, and eighth side 914 are fabricated from the elastomer. Alternatively, first side 202, second side 204, third side 206, and fourth side 302 are fabricated from the elastomer and fifth side 908, sixth side 910, seventh side 912, and eighth side 914 are fabricated from the shock-absorbing material. In an alternative embodiment, fifth side 908 is integral with first side 202. In another alternative embodiment, sixth side 910 is integral with second side 204. In yet another alternative embodiment, seventh side 912 is integral with third side 206. In still another alternative embodiment, eighth side 914 is integral with fourth side 302. In an alternative embodiment, shock absorber 900 includes at least one of fifth side 908, sixth side 910, seventh side 912, and eighth side 914. For example, shock absorber 900 does not include eighth side 914. In another alternative embodiment, shock absorber 900 does not include back side 402. In an embodiment of the invention, shock absorber 900 includes protrusion 802 on at least one of fifth side 908, sixth side 910, seventh side 912, and eighth side 914.

Protrusion 802 is formed on at least one of fifth side 908, sixth side 910, seventh side 912, and eighth side 914 in a similar manner in which protrusion 802 is formed on at least one of first side 202, second side 204, third side 206, and fourth side 302. For example, protrusion 802 extends from a top surface 918 of fifth side 908 to an intermediate point between top surface 918 and back side 402. As another example, protrusion 802 extends from fifth side 908 to an intermediate point between fifth side 908 and seventh side 912. Protrusion 908 is attached, such as bolted or glued, to one of fifth side 908, sixth side 910, seventh side 912, and eighth side 914. Alternatively, protrusion 908 is integral with one of fifth side 908, sixth side 910, seventh side 912, and eighth side 914.

Technical effects of shock absorbers 200, 300, 400, 700, and 900 include protecting detector 104 from abrasion by using the shock-absorbing material. Technical effects of protrusion 802 include preventing detector 104 from sliding by holding detector 104 in place. Other technical effects include providing shock absorbers 200, 300, 400, 700, and 900 that can be easily removed and cleaned. Sometimes the subject's blood deposits on at least one of shock absorbers 200, 300, 400, 700, and 900. Detector 104 can be easily separated from at least one of shock absorbers 200, 300, 400, 700, and 900 by manually removing housing 112 from at least one of shock absorbers 200, 300, 400, 700, and 900. Detector 104 is manually removed without using at least one of the electrical and mechanical tools. Other technical effects include providing a smooth surface by using the shock-absorbing material. The smooth surface provides comfort to the subject that touches the shock-absorbing material.

While the invention has been described in terms of various specific embodiments, those skilled in the art will recognize that the invention may be practiced with modification within the spirit and scope of the claims.

What is claimed is:

1. A shock absorber configured to couple to an exterior surface of a housing of a fully assembled medical imaging detector via a friction fit, said shock absorber comprising a frame removable from the housing of the fully assembled detector, said frame having three sides fabricated from at least one of plastic and metal wherein the three sides include a first side, a second side, and a third side, the frame is different from a housing, the second side located at an angle other than zero degrees from the first side, the third side located an at angle other than zero degrees from the second side, the second side is contiguous with the first side, and the third side is contiguous with the second side.

2. A shock absorber in accordance with claim 1 further comprising a fourth side contiguous with the third side and the first side.

3. A shock absorber in accordance with claim 1 further comprising:
   a fourth side contiguous with the third side and the first side; and
   a back side adjacent to the first, second, third, and fourth sides, the back side extending from the first side to the third side and from the second side to the fourth side.

4. A shock absorber in accordance with claim 1 further comprising a back side adjacent to the first, second, and third sides.

5. A shock absorber in accordance with claim 1 further comprising a back side adjacent to the first, second, and third sides, wherein the back side is fabricated from plastic.

6. A shock absorber in accordance with claim 1 wherein said shock absorber is configured to protect a portable detector.

7. A shock absorber in accordance with claim 1 wherein the frame is configured to be attached to the housing by a user without using at least one of a mechanical tool, an electrical tool, and an adhesive.

* * * * *